(12) United States Patent
Da Silva et al.

(10) Patent No.: US 7,963,959 B2
(45) Date of Patent: *Jun. 21, 2011

(54) AUTOMATED CRYOGENIC SKIN TREATMENT

(75) Inventors: Luiz Da Silva, Livermore, CA (US); Donald Cohen, Irvine, CA (US); Marc Lieberman, Carlsbad, CA (US)

(73) Assignee: Vandolay, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/617,565

(22) Filed: Nov. 12, 2009

(65) Prior Publication Data

US 2010/0087807 A1    Apr. 8, 2010

Related U.S. Application Data

(63) Continuation of application No. 12/575,370, filed on Oct. 7, 2009.

(60) Provisional application No. 61/103,285, filed on Oct. 7, 2008.

(51) Int. Cl.
*A61B 18/02* (2006.01)

(52) U.S. Cl. ............................. 606/23; 606/20; 606/22

(58) Field of Classification Search ............. 606/20–26; 378/65

See application file for complete search history.

(56) References Cited

U.S. PATENT DOCUMENTS

| | | | | |
|---|---|---|---|---|
| 5,531,740 | A | * | 7/1996 | Black .................................... 606/9 |
| 5,814,040 | A | | 9/1998 | Nelson et al. |
| 6,413,252 | B1 | | 7/2002 | Zavislan |
| 6,595,985 | B1 | | 7/2003 | Tobinick |
| 7,282,060 | B2 | * | 10/2007 | DeBenedictis et al. ......... 607/88 |
| 7,824,395 | B2 | * | 11/2010 | Chan et al. ...................... 606/10 |
| 2001/0009997 | A1 | * | 7/2001 | Pope et al. ......................... 606/9 |
| 2003/0216719 | A1 | * | 11/2003 | Debenedictis et al. ......... 606/10 |
| 2007/0005048 | A1 | | 1/2007 | Niedbala et al. |
| 2007/0118098 | A1 | * | 5/2007 | Tankovich ........................ 606/9 |
| 2007/0140426 | A1 | * | 6/2007 | Axelrod et al. ................. 378/65 |
| 2008/0154253 | A1 | | 6/2008 | Damasco et al. |

FOREIGN PATENT DOCUMENTS

WO    00/71044    11/2000

* cited by examiner

*Primary Examiner* — Michael Peffley
*Assistant Examiner* — Ronald Hupczey, Jr.
(74) *Attorney, Agent, or Firm* — Fish & Associates, PC

(57) ABSTRACT

An apparatus and methods for treating lesions on skin are presented. The apparatus collects information about a lesion and can automatically determine a course of treatment for the lesion. The device can include a controller that positions the nozzle proximate to a surface region of the lesion and automatically dispenses a pulse of the cryogenic fluid from the nozzle. The controller then positions the nozzle proximate to another surface region of the lesion and automatically dispenses a pulse of the cryogenic fluid from the nozzle.

16 Claims, 7 Drawing Sheets

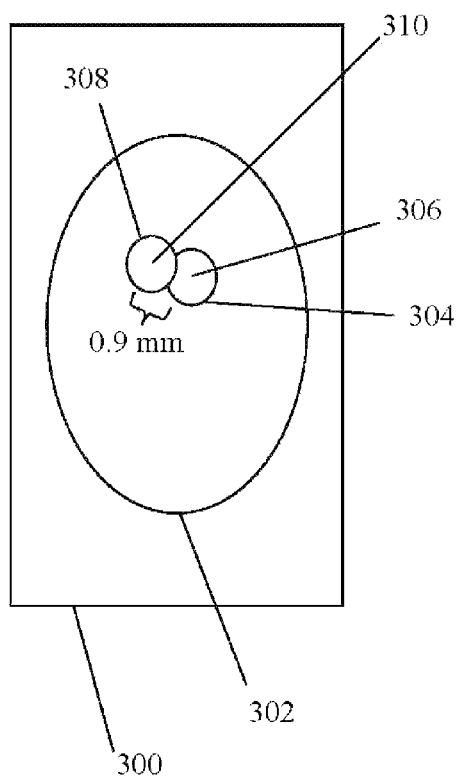 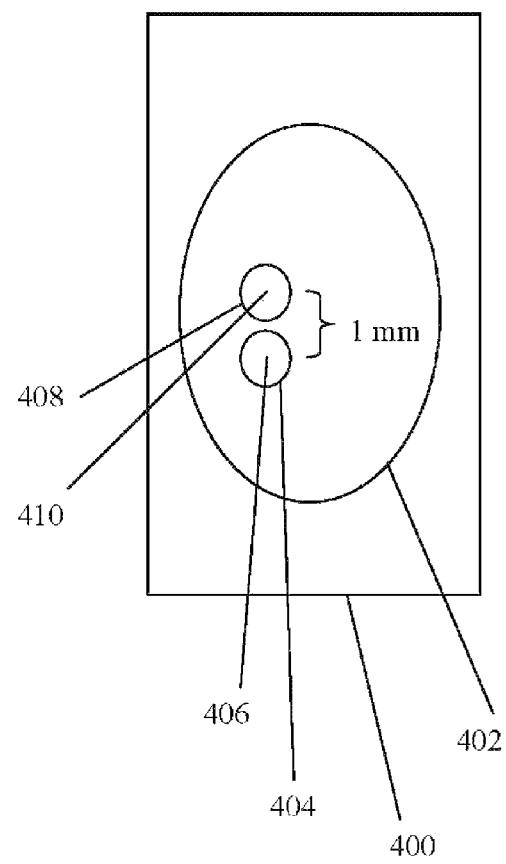
Figure 3                    Figure 4

AUTOMATED CRYOGENIC SKIN TREATMENT

This application is a continuation of co-pending U.S. utility application having Ser. No. 12/575,370 filed on Oct. 7, 2009, which claims priority to U.S. Provisional Application having Ser. No. 61/103,285 filed on Oct. 7, 2008. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is skin treatment technologies.

BACKGROUND

Many people seek skin treatment to improve the appearance of their skin, and particularly to reduce the discernible appearance of discolorations generally associated with aging. The skin conditions often targeted by such treatments include skin tags, moles, freckles, warts, actinic or seborrheic keratoses, angiomas and age spots (also known as liver spots), lentigines, or other skin-related abnormalities.

There are several types of procedures available that treat these skin conditions, ranging from topical ameliorations to more aggressive device treatments. Topical treatments include lotions, creams, acids, bleaching agents and vitamins. However, such treatments typically are slow, result in subtle improvement of the skin, may cause hypo- or hyper-pigmentation, and are often insufficient.

To provide a more complete treatment of the skin, it is known to use various optical device treatments (e.g., laser or other phototherapy). Such device treatments initially damage the target area, such that new skin proliferates after the healing process and generally improves the skin's appearance.

Optical device treatments typically include the use of lasers or other radiation to heat the skin or underlying tissue. For example, U.S. Patent Appl. No. 2008/0200908 to Domankevitz (publ. August 2008) discusses the use of the radiation to heat and thereby damage hair follicles. However, such radiation treatment can be painful for patients. In addition, such treatment is not precisely targeted to only treat the hair follicles. Instead, an area of skin with a plurality of hair follicles is flooded with the radiation until the follicles are damaged.

It is also known to use optical treatment devices to treat unwanted veins. For example, U.S. Pat. No. 5,522,813 to Trelles and U.S. Patent Appl. No. 2008/0071258 to Lemberg (publ. March 2008) discuss methods of treating veins using laser pulses laser to create holes or channels in the skin. However, such methods are problematic as they use the pulses to dig or pit into the skin, rather than attempt to dither (feather) the discoloration resulting from the treatments. In addition, such methods can leave scars on a patient.

Laser treatment devices have also been used to treat lesions. Such treatments are discussed in U.S. Patent Appl. No. 2007/0140426 to Axelrod (publ. June 2007), U.S. Patent Appl. No. 2007/0118098 to Tankovich (publ. May 2007), and U.S. Patent Appl. No. 2008/0009841 to Kuo (publ. January 2008).

The above laser treatments all suffer from similar disadvantages. Laser treatments often cause patients unnecessary pain or can scar the patient's skin. During laser treatment, scattering and absorption of the laser light often occurs in the skin tissue, which can cause significant changes in skin coloration and even scarring. In addition, laser treatments are often manually mediated, which can lead to mismatch of the flux of the laser to the spot. In addition, such manual mediation often leads to wide variation of treatment from one practitioner to the next.

To overcome some of the disadvantages of laser treatment, some practitioners currently use intense pulsed light (IPL) to treat lesions by damaging the unwanted tissue. An exemplary device is discussed in U.S. Patent Appl. No. 2008/0215124 to Wagenaar Cacciola, et al. (publ. September 2008). However, such IPL devices suffer from many of the disadvantages discussed above.

To avoid many of the disadvantages associated with optical treatment of the skin, various methods and device for cryogenic treatment are also known in the art, and such treatments generally involve the application of liquid nitrogen to a portion of the skin, such as by a spray or a cotton tipped applicator.

It has been reported that melanocytes freeze at −4 to −7° C. while surrounding squamous cells resist injury up to −20° C. Thus, it is possible to selectively treat lentigines without causing excessive damage to surrounding skin. When using cryogenic treatment, it is important to cool the treatment region to the proper temperature for an appropriate time. Cooling the region to too low a temperature can cause excessive damage. Cooling the region for too long a period of time can cause conduction of the cold temperature to neighboring tissue, increasing the size of the affected area. In addition, while surrounding tissue can survive a brief exposure to the very cold temperatures, prolonged exposure can cause tissue necrosis or excessive damage.

U.S. Pat. No. 6,226,996 to Weber et al. discusses a handheld device that includes a nozzle from which cryogenic fluid is sprayed on to the skin by a practitioner. The Weber device can be problematic as it simply sprays a cryogenic mist over the entire treatment area, which can lead to excessive or insufficient treating and cause hyper- or hypo-pigmentation of the skin. In addition, the Weber device requires manual movement and therefore lacks the ability to be positioned precisely over the desired treatment area, making it difficult to precisely control the temperature of the treatment area and surrounding skin, which often leads to inconsistent treatment.

U.S. Pat. No. 6,413,252 to Zavislan discusses a more complex treatment device that includes a confocal microscope to view sections of the treatment area. The area can be frozen by flooding the chamber above the area with a cryogenic fluid. However, the Zavislan device also utilizes a single pulse of cryogenic fluid to flood the entire treatment area, and suffers from the same problems as the Weber device discussed above.

Thus, there is still a need for a treatment apparatus that dispenses cryogenic fluid on a lesion at multiple regions of the lesion for a precise duration of time to cool the lesion and the surrounding skin to within a narrow temperature range.

SUMMARY OF THE INVENTION

The inventive subject matter provides apparatus, systems and methods in which an apparatus treats a lesion on an area of skin using a cryogenic fluid. In a preferred embodiment, the apparatus includes a controller, an image acquisition system, a nozzle that directs pulses of cryogenic fluid at the lesion, a positioner coupled to the nozzle, and a valve that allows cryogenic fluid to flow through the nozzle. Contemplated apparatus can preferably be used to treat skin of a patient's hand, though treating skin of the face, back or other areas are also contemplated.

As used herein, the term "lesion" means an area of abnormal tissue including, for example, age spots such as from a buildup of lipofuscin, warts, melasmi, lentigines, melanin, and other abnormal pigmentations or growths. As used herein, the term "cryogenic fluid" includes any commercially suitable fluid for contact with skin that can be cooled to a temperature below −5° C. including, for example, water, air, carbon dioxide, nitrogen, difluoroethane, dichloro difluoro methane, tetrafluoroethane, either alone or in combination. As used herein, the term "fluid" includes for example, liquids, gases, and some solids such as fluidized cryogenic pellets. As used herein, the term "pulse" includes spurts, sprays, pellets, or other fluid ejecta emitted in a short amount of time.

When the valve is opened, the cryogenic fluid flows from a cartridge to the nozzle, which directs the cryogenic fluid to a target region of the skin. All commercially suitable nozzle configurations are contemplated including, for example, straight through designs, converging designs, diverging designs, and coherent stream designs, either alone or in combination. Although preferred nozzles have a single entrance and exit, multiple entrances or exits are also contemplated (e.g., 3-way nozzles). The nozzle can advantageously create a coherent (e.g., collimated) stream or spray such that treatment of multiple regions of the lesion is consistent. However, it is also contemplated that non-coherent streams (e.g., divergent) could be used and controlled by adjusting the distance between the skin and the nozzle.

It is contemplated that a collimating nozzle is configured such that the diameter of the stream of cryogenic fluid from the nozzle remains approximately constant for about 25 mm from the nozzle. Thus, while the lesion to be treated is within 5 to 25 mm from the nozzle, the treatment intensity remains acceptably uniform and invariant.

In preferred embodiments, the nozzle is coupled to a positioner that is capable of moving in at least one, and preferably, multiple dimensions (e.g., in each of x, y and z planes). However, it is contemplated that the positioner could utilize polar coordinates rather than Cartesian. As used herein, the term "move" includes translation, tilting, and angling. An exemplary positioner includes a robotic arm to which the nozzle is coupled, such that the nozzle can be moved in three dimensions or with other degrees of freedom.

Especially preferred apparatus include one or more electronic image acquisition systems that examine the skin to acquire information about the lesion. An exemplary image acquisition system includes a USB video camera such as a Logitech® QuickCam® camera, which is connected to the controller or other processor either directly or indirectly. Contemplated image acquisition systems can be used to collect a variety of information about the lesion, including for example, measurements (e.g., surface area, height, and contours), colors, textures, and so forth. Preferred apparatus also include range finding apparatus to asses the contours of the skin and lesion, and to assess the distance from the nozzle outlet to the lesion. The apparatus could be radar, crossed light beams, stereo imaging, auto-focus or equivalent. Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

Although the image acquisition system and the nozzle could both be coupled to the positioner, it is also contemplated that the image acquisition system could be positioned separately from the nozzle either electronically by an additional positioner or manually, or could have a fixed position to view the treatment area.

Contemplated apparatus optionally, but preferably, includes a controller that uses the information collected by the image acquisition system to direct the dispensing of the cryogenic fluid. As used herein, the term "controller" can include one or more processors, sets of memory, or other computer hardware. An exemplary controller is a personal computer or its equivalent. Although preferred controllers are arranged in a single housing, it is contemplated that various components of the controller could have separate housings.

In some embodiments, after the controller receives the information collected by the image acquisition device, the controller preferably analyzes the information to identify the type and boundaries of lesions on the skin. The controller preferably utilizes a processor and software to analyze the image and other information about the lesion. For example, the controller could use the software to determine an average reflection intensity of the skin for a single waveband with essentially flat illumination, and identify the borders of areas of skin where the pixels deviate from an average reflectance value by more than a predetermined percentage. As another example, the processor could utilize edge detection software to identify position of the patient's hand, as well as the color and intensity of the skin surrounding the lesion. Thus, the areas of the hand in which the color and intensity deviate from normal can be identified.

The boundaries of the lesions can be tagged for possible treatment, and a course of treatment can be determined. Imaging can be performed at multiple wavelengths to enhance contrast and improve detection. Alternatively, white light illumination can be combined with a color imaging sensor to measure absorption and scattering at specific wavelengths.

It is contemplated that at least some portion of the processing and analysis of the information could alternatively be performed by the image acquisition system.

Once the lesions have been identified, the controller can utilize software to determine a course of treatment for each of the lesions as well as an overall course of treatment for the patient. Such courses of treatment are preferably optimized within each of the courses of treatment and for the entire treatment overall.

Contemplated courses of treatment include subdividing each of the lesions into two or more regions that might or might not overlap, with each region receiving at least one pulse of cryogenic fluid. The course of treatment specifies the spot sizes and duration of the cryogenic fluid pulses, the number of pulses, the rate of pulsation of the cryogenic fluid, the centers of each pulse, the wait time between pulses, and a dispensing pattern. It is contemplated that the attributes of each pulse can be varied from that of other pulses. In addition, contemplated exposure time for the lesion can be adjusted depending on physical or chemical properties of the fluid.

A preferred course of treatment includes a plurality of pulses each having a duration of less than one seconds, and more preferably less than 200 ms. The centers of each region at which the pulses are dispensed can advantageously form a pattern such that any discoloration resulting from the treatment is feathered across the lesion or beyond. Preferably, the centers of the first and second regions are within 5 mm of one another, and more preferably, 2 mm of one other, though even centers less than 1 mm apart are contemplated.

In one embodiment, the course of treatment produces a pixelated pattern having a greater density of pulses near the center of the lesion likely from a larger number of overlapping regions. As the distance of each region's center from the lesion's center increases, the density of pulses will decrease. Alternatively, it is contemplated that one or more nozzles can utilize a mask or other pulse distribution that allows the distribution of the cryogenic fluid in each pulse to be greater near the center of the lesion. Such distribution can also be accomplished by using variable duration pulses or multiple nozzles, such as to create concentric distributions of cryogenic fluid on the lesion and thereby weight the distribution of fluid toward the center of the lesion.

Preferably, the pulses are separated by no more than 30 seconds, though it is especially preferred that the pulses are separated by no more than 20 or even less than 10 seconds. It is contemplated that the first and second pulses could be separated by as little as 10 milliseconds. The time between each pulse can be adjusted according to the distance between the centers of the region and the properties of the cryogenic fluid. Thus, for example, regions that overlap may require a longer period between pulses than regions that do not overlap. By minimizing the duration of the pulses, any pain or discoloration (e.g., hyper- or hypo-pigmentation) of the skin can be limited.

It is especially preferred that the time between pulses is kept to a minimum effective duration such as by optimizing the courses of treatment for each lesion. For example, it is contemplated that the overall course of treatment for the patient might be optimized such that treatment of a second lesion can begin prior to the completion of the course of treatment for the first region.

The typical lesion to be treated will be irregular in shape and several millimeters across. It is preferred that the lesion is divided into a plurality of surface regions that may or may not overlap. Although preferred regions have a surface area of no more 2 sq. mm, the sizes and dimensions of the regions will vary depending on the size of the apparatus, the size of the lesion, and the type of lesion to be treated. For example, using a series of adjacent treatment regions that are separated from their centers by approximately 2 mm subjects the lesion and the surrounding skin to only slight variations in treatment intensity with minimal discontinuities.

It is further contemplated that the apparatus could include high power LEDs, lasers, or other optical devices to treat the lesion.

In one aspect, a method is provided for treating an age spot with the machine, in which the machine is used to locate the age spot, and the machine automatically dispenses pulses of a fluid to each of at least three different regions of the age spot. Preferably, each of the regions are separated by a short distance (e.g., no more than 2 mm), and each of the pulses are separated by no more than 30 seconds.

Prior to dispensing each of the pulses, the machine can automatically position a nozzle at a center of one of the at least three regions. Ideally, the machine would position the nozzle at a center of a first region prior to dispensing the fluid, and then position the nozzle at a center of a second region, prior to dispensing a subsequent pulse of the fluid. When the cryogenic fluid touches the region of the skin, its temperature is preferably no warmer than −5° C.

Optionally, the method could include using the machine to detect motion of any of the regions, and triggering an alteration in the dispensing of the fluid, such as by moving the nozzle to compensate for the movement of the region or by interrupting flow. Such movement might be translation or angular movement of the nozzle.

The machine can preferably at least partially differentiate among at least two of a lentigo, a skin tag, a mole, a wart, a keratosis, acne, leukoplakia, or other lesion. This is advantageous as such a machine would be able to accurately diagnose what lesion or lesions are present on a patient's skin, ensuring a proper course of treatment is applied.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 4 illustrates a lesion on a patient's skin where the treatment regions do not overlap.

FIG. 3 shows a lesion on a patient's skin where the treatment regions overlap.

DETAILED DESCRIPTION

Figure 1:
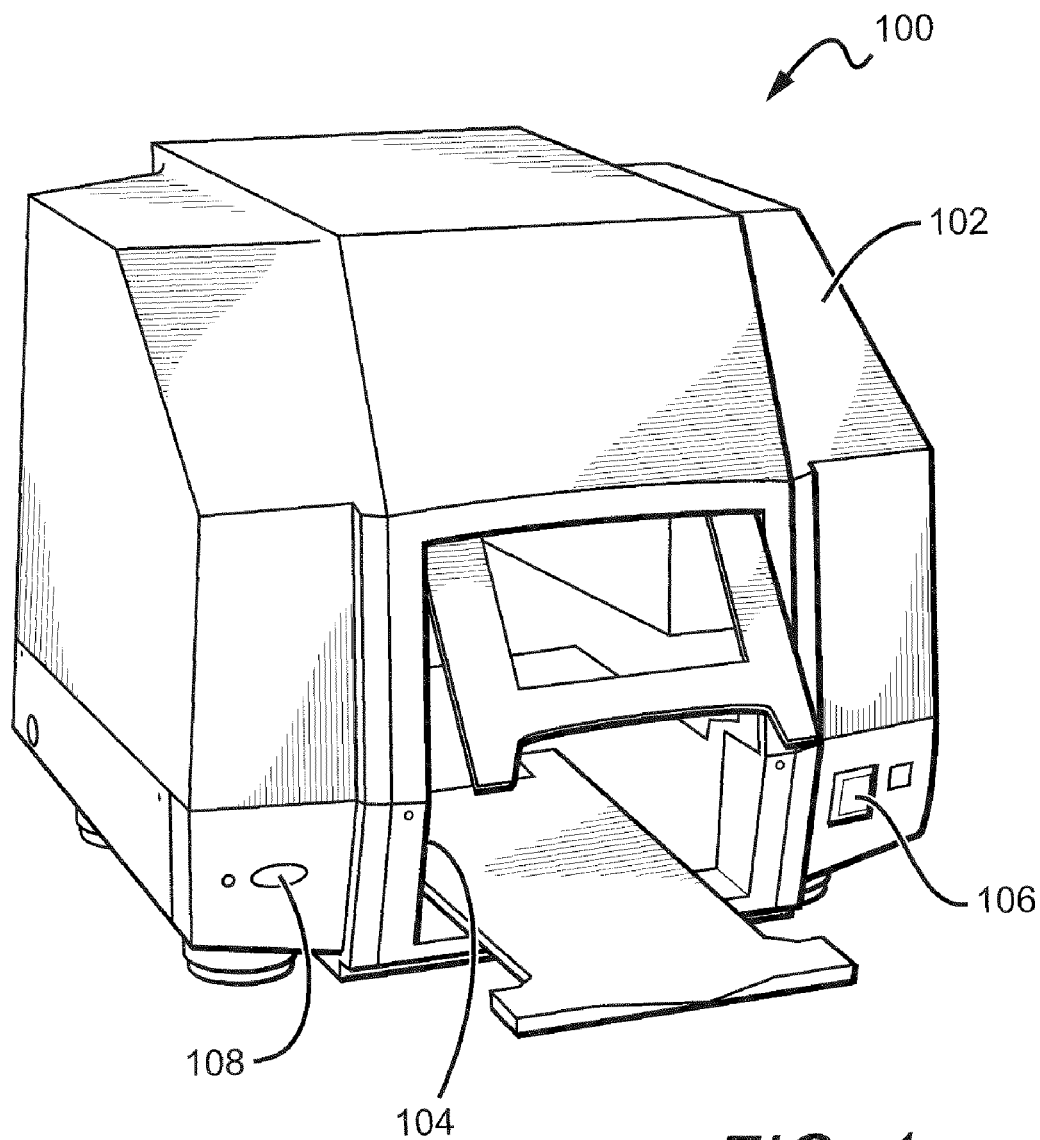
FIG. 1 presents an example embodiment of a skin treatment apparatus.

The following description discusses inventive concepts with respect to treating a patient's right or left hand. One should appreciate that the techniques can be equally applied to other areas of a patient's skin. In addition, the techniques described herein could be applied to animals, plants and so forth.

Overview

The apparatus discussed herein utilize one or more cryogenic fluids to treat a lesion on a patient's skin. Though preferred cryogenic fluids are cold at standard pressure, it is also contemplated that the cryogenic fluid could alternatively be cooled or heated as needed prior to being dispensed through the nozzle. Additionally, or alternatively, the cryogenic fluids could be cooled through expansion after exiting a nozzle, as is consistent with reduction of pressure of a gas. In some embodiments the fluid can be recaptured or recycled.

The rate at which the pressure of the fluid impinging on the skin rises can be controlled by appropriate pulsing of a valve, such as a solenoid valve. Similarly the rate at which the pulse pressure is terminated can also be controlled. For example, it is contemplated that the rise rate and decay rate for a pulse can each be greater than 100 psi/second. This is particularly useful for treatments in which it is desirable to acutely remove tissue rather than lyse it in-situ.

The cryogenic fluid is preferably pressurized. Such pressure could be provided by the vapor pressure of the cryogenic fluid, or alternatively, the cryogenic fluid could be charged to a higher pressure using air, nitrogen, carbon dioxide, argon or other innocuous gas. In addition, the pressure could be provided with a mechanical, hydraulic, pneumatic or other equivalent system.

It is preferred that the cryogenic fluid resides in a disposable cartridge or other housing, though contemplated cartridges could be refillable. It is contemplated that the apparatus could include two or more cartridges of cryogenic fluid, with the cartridges containing the same or different cryogenic fluids such as to treat different types of lesions or to be mixed in treating a single lesion.

Preferred cryogenic cartridges can contain a check valve or other commercially suitable valve that is normally closed while the cartridge is in transit or storage. Once the cartridge is connected to the apparatus, the valve is opened. The cartridges could advantageously be configured to ensure that the cartridges are authorized for use in the apparatus. Such configurations could include, for example, proprietary interlocks, various circuitries, specific sizes and dimensions, keys, or other authorization schemes.

Flow of the cryogenic fluid from the cartridge to the nozzle can be controlled by a 2-way solenoid valve, though all commercially suitable valves are contemplated including, for example, ball valves, butterfly valves, check valves, diaphragm valves, gate valves, globe valves, needle valves, plug valves, either alone or in combination. Although the valve could be manually operated such as by a practitioner, it is preferred that the valve is electronically controlled by a controller. Rather than utilize a solenoid to actuate the valve, a piezoelectric system could also be used.

Preferably, the valve is open only when the positioner is stationary, though in some contemplated embodiments, the valve could be opened while the positioner is in motion. In such embodiments, the exposure intensity of the fluid on a skin area can be controlled by varying a speed or direction at which the positioner scans the cryogenic nozzle over the area of interest.

Contemplated apparatus can further include one or more thermistors at various positioners between the cryogenic fluid source and the nozzle, such that the temperature and flow of the cryogenic fluid can be monitored. This helps ensure proper functioning of the apparatus and thereby ensures proper results from the pulses on the lesion. It is preferred that the cryogenic fluid temperature is no warmer than $-5°$ C. at the skin. In other embodiments, the thermistors could be replaced by other temperature sensors such as thermocouples, infrared thermometers, and so forth. Alternatively or additionally, the temperature sensor could be replaced by a flow sensor to allow calculation of heat transfer.

In especially preferred embodiments, the apparatus includes a rotating mechanism that allows an appendage containing the lesion to be rotated as needed for precise application of the cryogenic fluid. For example, a hand having a lesion could hold a grip during treatment, and the grip could be rotated such that the lesion on the hand is also rotated. Alternatively, the palm of the hand could be placed on a sphere-like structure that can be rotated to thereby rotate the patient's hand. For a larger area of a patient's body, it is contemplated that a table, gimble or other platform on which the patient or a patient's appendage rests can be rotated to thereby rotate the lesion.

In another aspect, a method of treating a lesion of a patient's skin is provided using a controller that at least partially automates the treatment. An image is acquired of the patient's skin using an image acquisition system. The image acquisition system or the controller analyzes the image to determine a region of the skin to be treated. The controller can direct the positioner to move the nozzle proximate a first surface region of the lesion, and automatically directs a first pulse of the cryogenic fluid to be dispensed at an upper surface of the first surface region (i.e., normally facing toward the air and away from the dermis). As used herein, the term "proximate" means functionally close enough to effect a desired change in the region resulting from dispensing the pulse of cryogenic fluid.

The nozzle can then be directed to a second surface region of the same lesion, at which point a second pulse of cryogenic fluid can be dispensed at an upper surface (i.e., normally facing the air and away from the dermis) of the second surface region. The dispensing of the first and second pulses can either be directly controlled by the controller or indirectly controlled such as at the direction of the controller to a valve or valve actuator. Similarly, the positioning of the nozzle can also be directly controlled by the controller, or indirectly controlled such as at the direction of the controller to the positioner or other device. Though the first and second regions are preferably treated in a uniform manner (i.e., using pulses having similar attributes), it is contemplated that each of the pulses could have different attributes.

Apparatus

In FIG. 1, apparatus 100 can comprise a housing 102 having an opening 104 into which a hand of a patient (not shown) can extend. The housing 102 includes a power switch 106 and an activation button 108 that activates the apparatus 100 to analyze and treat lesions on the patient's hand.

Figure 2:
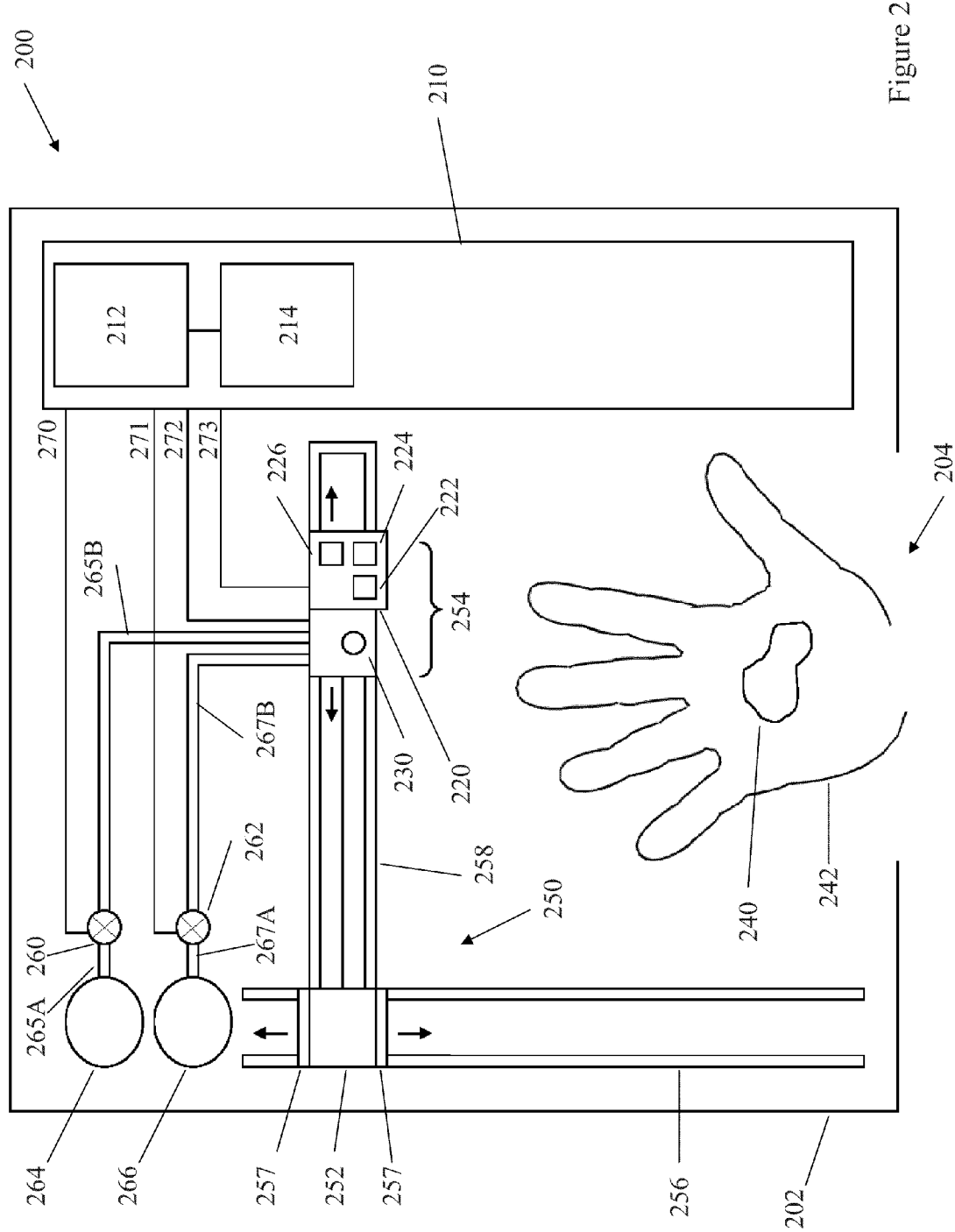
FIG. 2 presents a top plan view of an embodiment of a skin treatment apparatus.

FIG. 2 illustrates a housing 202 of an apparatus 200 having a controller 210, an image acquisition system 220, a nozzle 230 that directs pulses of cryogenic fluid at a lesion 240, a positioner 250 coupled to the nozzle 230, and first and second valves 260 and 262 that allows cryogenic fluid to flow from first and second cartridges 264 and 266, respectively, to the nozzle 230.

Although preferred apparatus include the various components within a single housing, it is contemplated that some or all of these components could be remote from the apparatus. Thus, for example, the controller 210 could have a separate housing from the apparatus 200, and be coupled to the apparatus 200 by a wired or wireless connection.

Housing 202 can include an opening 204 into which a hand 242 of a patient can extend. It is contemplated that the housing 202 or the opening 204 could be configured such that other areas of a patient's skin could be treated. For example, the housing and opening could be configured to receive a patient's entire body.

That apparatus can have one or more positioners to position the nozzle, image acquisition system or other components of the apparatus by the lesion. It is contemplated that positioner 250 can include first and second portions 252 and 254 that allow positioner 250 to move within the limits of its degrees of freedom. As shown, positioner 250 can move in three cardinal dimensions. The first portion 252 of the positioner 250 moves along tracks 256 in a y direction. In addition the first portion 252 moves up and down along tracks 257 (i.e., in and out of the page). The second portion 254 moves along tracks 258 that are coupled to the first portion 252. In this manner, positioner 250 can move the nozzle 230 and the image acquisition system 220 in three directions. Rather than a series of tracks, other configurations of positioners are contemplated including, for example, one or more robotic arms.

The positioner 250 can move the nozzle 230, and flexible pipes 265A-265B and 267A-267B or other tubing can couple the first and second cartridges 264 and 266 of cryogenic fluid to respective first and second valves 260 and 262 and to nozzle 230. Alternatively, the nozzle 230 could be fixed in place while the lesion 240 is positioned proximate to nozzle 230, such as by moving that portion of the patient or a patient's entire body. The positioner 250 could further include a cartridge (not shown) having cryogenic fluid to be dispensed through the nozzle 230.

Rather than first and second cartridges 264 and 266, it is contemplated that a single cartridge (not shown) or three or more cartridges could be used in the apparatus 200. Additionally or alternatively, apparatus 200 could be fed the cryogenic fluid from a source external to the apparatus 200. It is also contemplated that the cryogenic fluid could be disposed in any commercially suitable container.

Alternatively or additionally, the positioner 250 could position or angle the nozzle 230 as necessary to properly align the nozzle 230 with the lesion 240. The nozzle 230 can optionally be rotatably coupled to the positioner 250 such that the nozzle's angle of attack can be varied. The positioner 250 can preferably be electronically controlled such as by the controller 210, which advantageously allows the nozzle 230 to be precisely positioned proximate to the lesion 240. Alternatively or additionally, the positioner 250 could be manually controlled where a technician or other user can override the position to allow for manual orientation of the positioner 250.

Apparatus 200 could further include additional nozzles (not shown) such that a dual or concentric spray (e.g., the second nozzle is broader than the first) can be provided. Such additional nozzles could be used concurrently or separately from the first nozzle 230. Thus, for example, the additional nozzle(s) could produce differently shaped sprays from that of the first nozzle 230. Such additional nozzles could dispense a pulse of cryogenic fluid having different attributes from pulses of the first nozzle 230. The additional nozzles could also be used to dispense a second cryogenic or other fluid including, for example, a cryogenic therapeutic agent, a facilitating material or a healing/soothing agent. It is contemplated that the additional nozzles could be disposed on a rotatable head, such that the attributes of the pulse could be varied by rotating the head and thereby changing the nozzle to be used.

Housing 202 includes first and second cartridges 264 and 266 that each contains a cryogenic fluid. In some commercial embodiments, the first cartridge 264 contains tetrafluoroethane and the second cartridge 266 contains liquid nitrogen, although other commercially-suitable cryogenic fluids could be substituted for one or both of the cryogenic fluids.

The first cartridge 264 is coupled to the first valve 260 by piping 265A. The first valve 260 is coupled to the nozzle 230 by piping 265B. Similarly, the second cartridge 266 is coupled to the second valve 262 by piping 267A, and the second valve 262 is coupled to the nozzle 230 by piping 267B. Alternatively, each of the first and second valves 260 and 262 could be coupled together using a Y-junction which is then coupled to the nozzle 230. In other contemplated embodiments, the first and second cartridges 264 and 266 could be coupled to a respective first and second nozzle (not shown).

Controller 210 includes a processor 212 and memory 214 such as for storing software, information collected by the image acquisition system, and courses of treatment for different lesions. While controller 210 is shown enclosed within housing 202, it is also contemplated that at least part of controller 210 could be disposed remote from housing 202.

Controller 210 is wired to each of the first and second valves, the image acquisition system 220 and the positioner 250 by wired connections 270-273, although wireless connections are also contemplated. Any commercially suitable wired connections (e.g., USB, Firewire, Ethernet, IP over power lines, RS-232, RS-485, and DAQ I/O board) or wireless connections (e.g., WI-FI, infrared, Bluetooth, and radio frequency) can be used. Thus, for example, the controller 210 could wirelessly interface with the image acquisition system 220 while having a wired interface with the positioner 250. It is preferred that the any break in the connection between the controller 210 and its coupled components causes the apparatus 200 to shut down or retract to a safety position.

In this manner, the controller 210 can obtain information collected by the image acquisition system 220 and historical records of efficacy, and use such information to determine a course of treatment for the lesion. The controller 210 can also position the nozzle 230 or image acquisition system 220 as desired, and dispense a pulse of cryogenic fluid from either or both of the first 264 and second cartridges 266 by opening the first 260 or second valves 262.

Controller 210 can preferably be configured to update its firmware over a network. Additionally, controller 210 could also obtain additional treatment plan information, patterns, identification algorithms, or other treatment related information over the network. It is contemplated that best practices could evolve over time. Therefore, it would be advantageous to allow controller 210 to be updated to reflect changes in treatments.

Preferably, controller 210 can alter the pulsation of the cryogenic fluid with respect to at least one of frequency, duty cycle, pulse shape, amplitude, rate, dispersion, diameter of the cryogenic fluid stream, convergence, divergence, collimation or other attributes. Additionally or alternatively, a practitioner could alter the configuration of the pulses.

Image acquisition system 220 includes camera 222 that captures an image of the lesion 240. However, the image acquisition system could alternatively have one or more sensors including, for example, video cameras, still cameras, infrared, linear optical arrays, stereo optic imaging equipment, or other commercially suitable sensors, either alone or in combination. Preferably, the image acquisition system 220 is stereoscopic.

Image acquisition system 220 includes a processor 224 that uses software stored in memory 226 to analyze the information collected about the patient. The image acquisition system 220 can identify the type of lesion 240 on the hand 242 or other area of skin, and determine a course of treatment for the lesion 240 at least partially based upon the information gathered. Such course of treatment could also be at least partially based upon historical treatment data of the patient. As used herein, the term "determine" includes simply providing a suggested treatment to a practitioner or other user, as well as automatically establishing and carrying out a course of treatment, possibly either directly or indirectly such as by the controller. This analysis can then be transmitted to controller 210.

Alternatively or additionally, the image acquisition system could transmit the information about the lesion to the controller 210 for analysis by the controller 210. In such cases, the controller 210 could then determine a course of treatment and direct the treatment automatically or at the request of a practitioner. In such cases, it is not essential that the image acquisition system include a processor or memory.

Apparatus 200 can preferably include lighting (not shown) such as by several light emitting diodes (LEDs) or other commercially suitable lights. Such lighting advantageously allows the lighting of the lesion is flat, bright and consistent, which helps to eliminate shadows on the skin that could be mistaken for skin discolorations or other abnormalities. It is further contemplated that the image acquisition system can include one or more additional sensors capable of highlighting or enhancing lesions. For example, the image acquisition system 220 could include a polarized light source and a sensor with a cross polarized filter to detect and emphasize the reflectance of the light that has interacted with the skin and record images of the lesion 240 at various polarizations to assist in evaluating skin type and structure. Multiple light sources with different polarization angles could be used for more accurate analysis of skin type and structure.

Controller 210 receives the analysis from the image acquisition system 220, and determines a course of treatment of lesion 240 that is at least partially based on the analysis.

The apparatus 200 can also advantageously include sensors (not shown) to monitor the temperature and flow rate of the cryogenic fluid, such that the magnitude of a treatment can be measured. The apparatus 200 can further include sensors that monitor a position of the lesion 240 such that the nozzle 230 could be repositioned as necessary to compensate for any unexpected movement of the lesion 240 (e.g., movement of the patient prior to, or during, the treatment).

In FIG. 3, a portion of a patient's skin 300 is shown that contains lesion 302. First and second regions 304 and 308 of the lesion are shown which partially overlap. Likewise, FIG. 4 shows a portion of a patient's skin 400 that contains a lesion 402. The lesion has been treated with first and second non-overlapping regions 404 and 408. The respective centers 406 and 410 of the first and second regions 404 and 408 are less than 1 mm apart.

Figure 5:
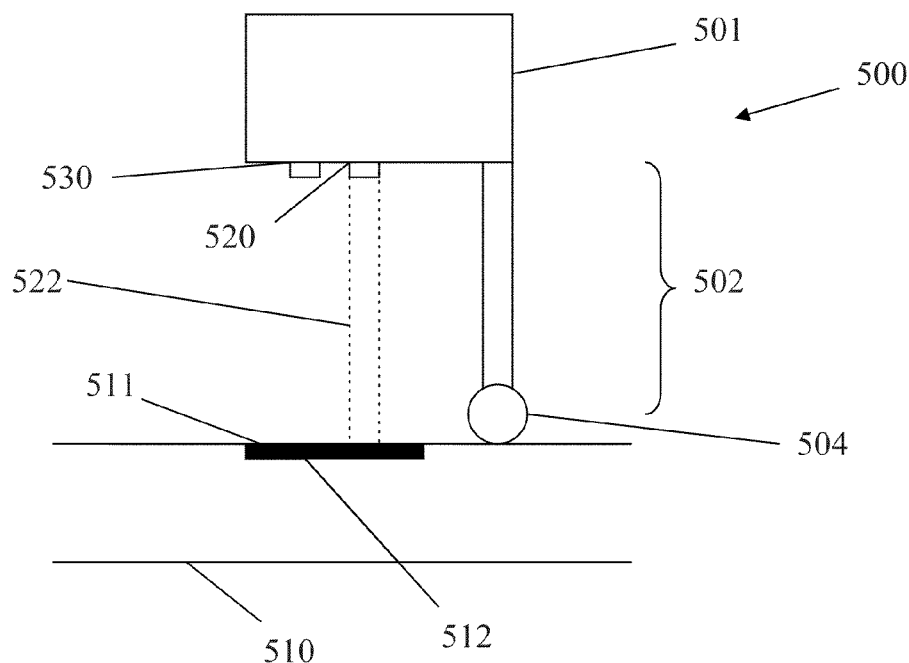
FIGS. 5-8 show various embodiments of a positioner having nozzles and other components.

In FIG. 5, apparatus 500 includes a positioner 501 that has a spacer 502 to maintain a nearly constant distance, and preferably a distance of less than 10 mm, between the nozzle 520 and lesion 512. The spacer includes a wheel 504, ball, or similar mechanism at one end such that the spacer 502 can roll along the patient's skin 510. Positioner 501 includes nozzle 520 and image acquisition device 530. The nozzle 520 is shown dispensing a first pulse 522 of cryogenic fluid at an upper surface 511 of the lesion 512. The spacer 502 can include, for example, spring loaded casters, sliders, and so forth.

Figure 6:
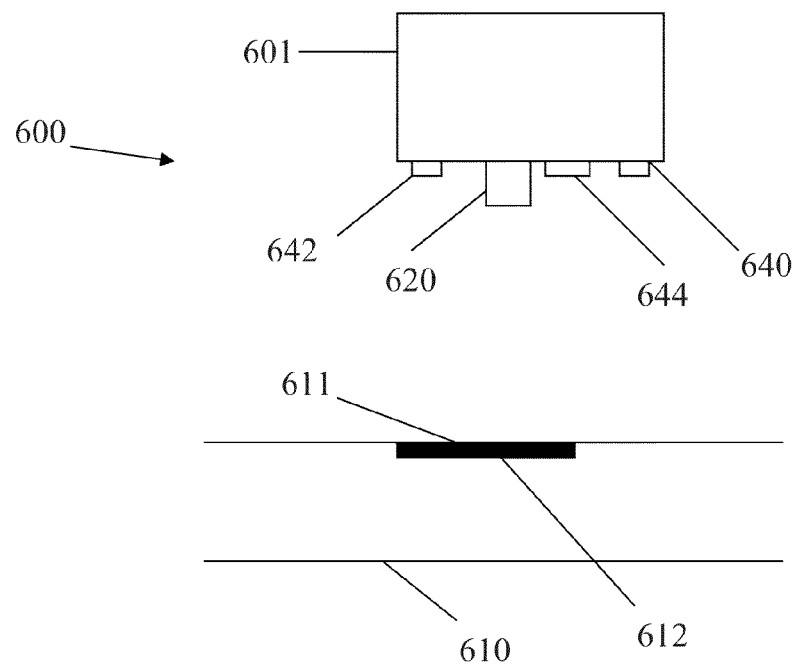

In FIG. 6, apparatus 600 includes a positioner 601 that has a nozzle 620, optical beam emitters 640 and 642 that each directs an optical beam at an upper surface 611 of the lesion 612. A sensor 644 detects the reflectance of the optical beams from an upper surface 611 of lesion 612 on a patient's skin 610. Z-axis information can be produced and transmitted to the controller (not shown) such that a near constant distance can be maintained between the nozzle 620 and the lesion 612. Alternatively, sonar or other commercially suitable systems for measuring the distance could also be used.

Figure 7:
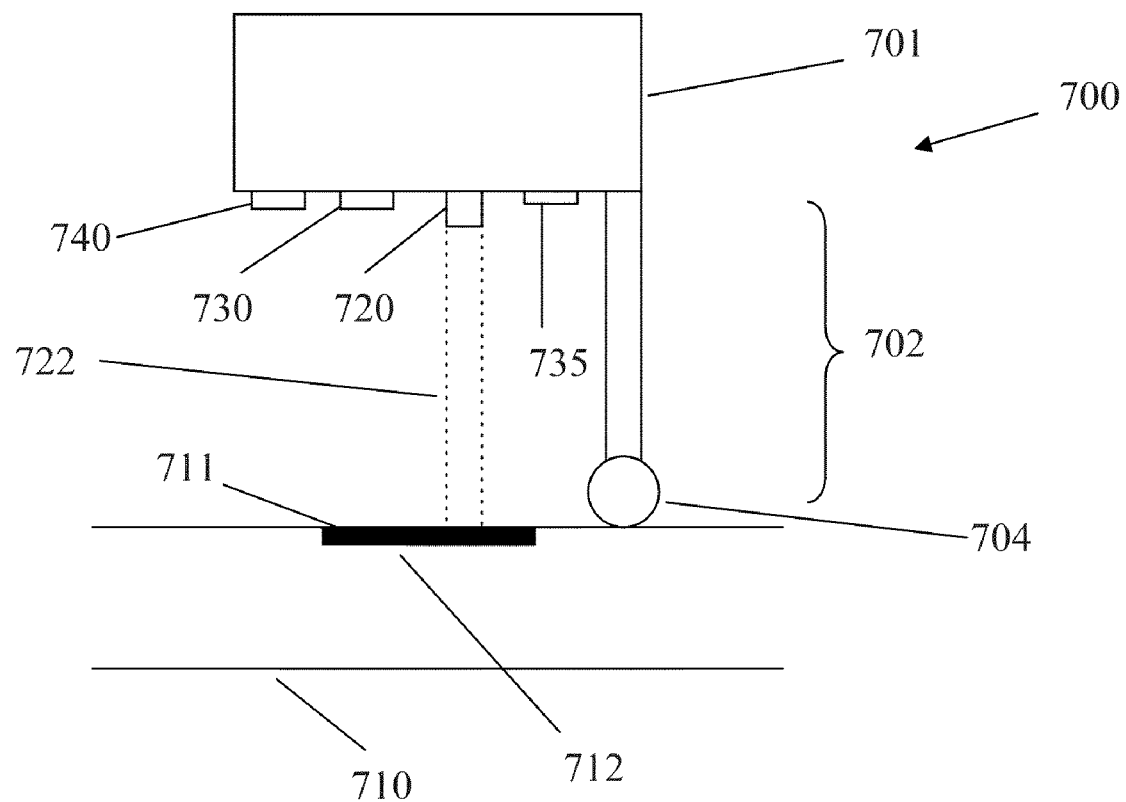

FIG. 7 illustrates another embodiment of a positioner 701 of an apparatus 700 that includes nozzle 720, a temperature sensor 730, or a coloration sensor 740. The temperature sensor 730 or coloration sensor 740 can be used to monitor a change in at least one of a coloration and a temperature the lesion 712. This is advantageous as temperature sensor 730 or coloration sensor 740 can provide a safety shut off in case the lesion 712 is inadvertently exposed to a higher level of cryogenic fluid than desired. In addition, the information from such sensors 730 and 740 can provide feedback to a controller (not shown), which allows the controller to dynamically update the course of treatment of the lesion 712 including, for example, the number of regions to be treated, the position of the regions on the skin, the total exposure of the regions and the lesion to the cryogenic fluid, and various attributes of the cryogenic pulses.

Apparatus 700 can also include a motion sensor 735 to detect motion of the lesion 712 or surrounding skin 710. This is advantageous as information from the motion sensor 735 can be used to provide a safety shut off to prevent cryogenic fluid from being dispensed at an incorrect location of the skin. In addition, the information from the motion sensor 735 can provide feedback to a controller (not shown), which allows the controller to dynamically update the course of treatment of the lesion 712 including, for example, the position of nozzle 720. With respect to the remaining numerals in FIG. 7, the same considerations for like components with like numerals of FIG. 5 apply.

Figure 8:
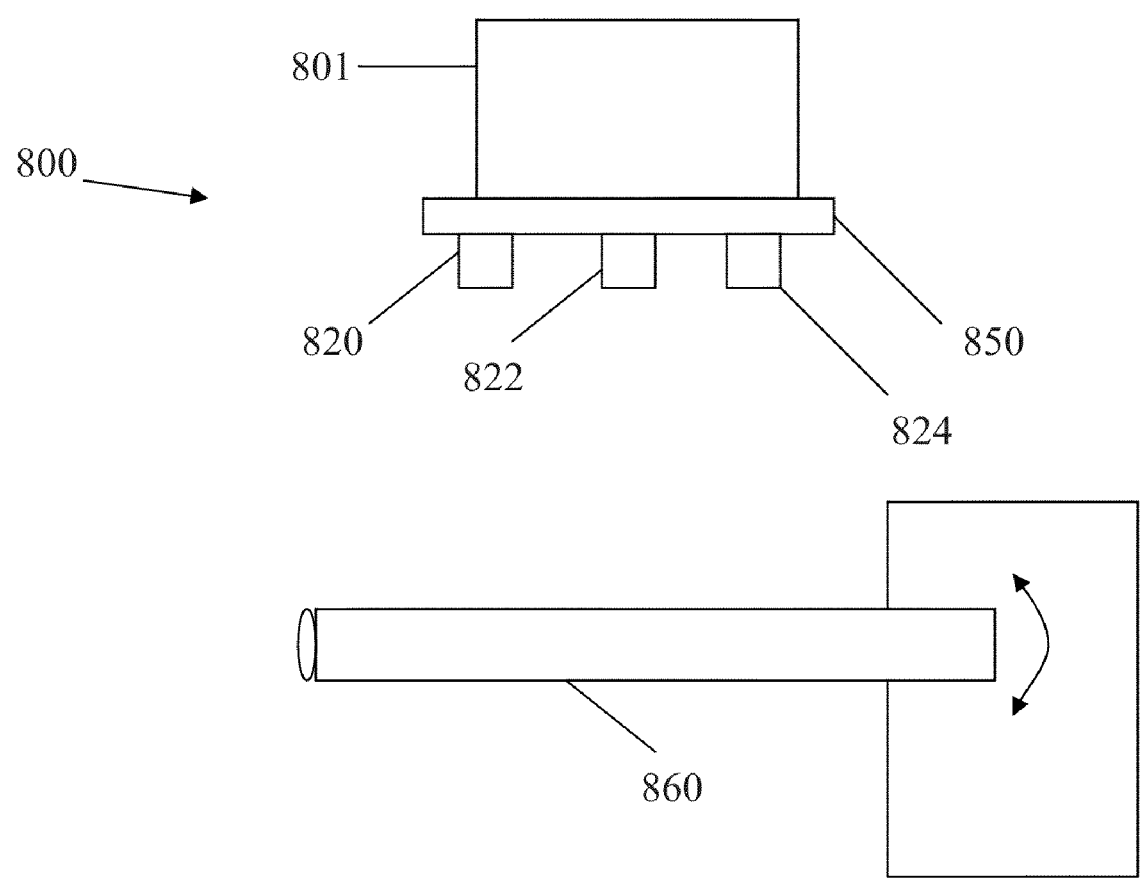

In FIG. 8, apparatus 800 includes a positioner 801 that has nozzles 820, 822 and 824 that are disposed on a rotatable head 850, such that a specific nozzle can be chosen prior to dispensing a pulse of a cryogenic fluid. It is also contemplated that a controller (not shown) could be used to rotate the head 850 and thereby rotate the nozzles 820, 822, and 824. It is preferred that each of nozzles 820, 822, and 824 dispenses a pulse having attributes different from pulses dispensed by the other nozzles.

Apparatus can also include a rotatable grip 860 or other rotating mechanisms that allows an appendage (not shown) to be rotated as needed for precise application of a cryogenic fluid. For example, a hand having a lesion could hold grip 860 during treatment, and the grip 860 could be rotated such that the lesion is thereby rotated.

Figure 9:
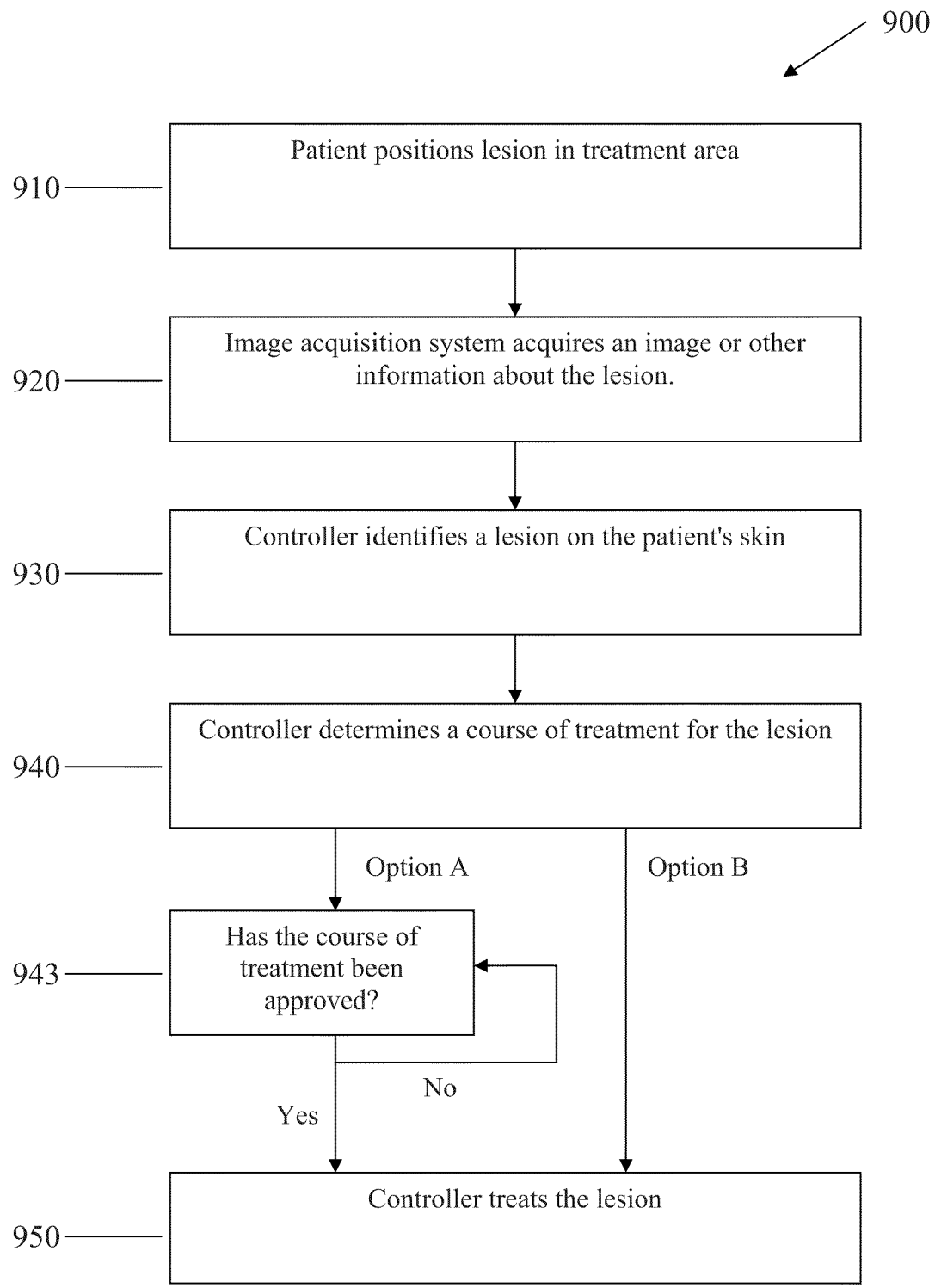
FIG. 9 presents a flow chart of a method for treating a lesion on a patient's skin.

In FIG. 9, a flow chart illustrates the various steps of an embodiment of treating a lesion, especially an age spot, with a machine 900. Before the treatment can begin, a patient's hand containing a lesion is positioned in a treatment area 910, preferably within the housing of the machine. An image or other information about the lesion is then acquired by an image acquisition system 920, and such information can be transmitted to a controller for analysis.

The controller identifies lesions on the skin 930, and optionally determines a course of treatment for each of the lesions 940. The apparatus can be configured to await approval of the course of treatment by a practitioner to allow the practitioner to modify the course of treatment 943. Alternatively, the determined course of treatment could be automatically carried out without requiring approval of the practitioner.

Where the controller awaits approval of the course of treatment, the boundaries of each of the lesions can be displayed on a monitor such that a practitioner can accept, modify, or reject the determined course of treatment of the lesions.

Once the operator accepts the course of treatment or the course is automatically initiated 950, the valve is opened until a thermistor indicates that the nozzle is chilled to a temperature below $-5°$ C., and the system is primed so that the cryogenic fluid fills the tubing.

The controller then directs the positioner to move the nozzle proximate to a first region of an upper surface of the lesion, and the controller then reopens the valve and cryogenic fluid is dispensed from the nozzle. After the first pulse of cryogenic fluid, the nozzle is moved by the positioner proximate to a second region of an upper surface of the lesion. Preferably, each region of the lesion is exposed to a precisely metered pulse of cryogenic fluid, where "precisely metered" means a pulse that is within about 1 ms of the specified pulse duration, and within about 0.5 mm of the specified pulse diameter. In this manner, exposure of the lesion to the cryogenic fluid is consistent to a degree not achievable with a manually directed treatment.

The course of treatment continues until either the treatment is completed, or a signal from a sensor indicates that the treatment is sufficient. Such sensors could continually monitor various characteristics of the lesion including, for example, color, temperature, and so forth. Such monitoring could alternatively occur between pulses such as to provide more accurate readings.

The position of the hand, and thus the lesion(s), can be confirmed periodically by analyzing images obtained by the image acquisition system. Should any excessive hand motion be detected, the treatment could automatically be disrupted such that only specific regions of the lesion would be treated. Alternatively, the nozzle or skin of the patient could be repositioned as necessary to compensate for the hand motion.

At the boundaries of lesion, the cryogenic exposure is advantageously reduced to thereby "feather" or dither the treatment intensity. This serves to blend any disparities between the appearance of the treated skin and the untreated skin. Preferably, the feathering can be achieved by reducing the time that the lesion is exposed to the cryogenic fluid such as by using shorter solenoid pulse durations on outer regions, than the pulse duration used on regions near the center of the lesion. Alternatively, this could be accomplished by other processes such as by applying an identical pulse of a divergent cryogenic fluid stream where the nozzle is further from the lesion at regions away from the center of the lesion.

It is contemplated that a patient could utilize repeat treatments to further improve results. Such treatments are contemplated to be performed at any time after the prior treatment including immediately after or even years later.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An apparatus for treating a lesion of an area of skin using a cryogenic fluid, comprising:
   a dispensing nozzle configured to dispense the cryogenic fluid;
   a valve that regulates flow of the cryogenic fluid to the nozzle;
   a positioner disposed to move the nozzle;
   an electronic image acquisition system that examines the skin to acquire information about the lesion;
   a controller programmed to use the information to determine a sequential, multi-pulsed course of treatment for the lesion, in which the device automatically dispenses a first pulse of the cryogenic fluid at a first surface region of the lesion, automatically redirects the nozzle, and then dispenses a second pulse of the cryogenic fluid at a second surface region of the lesion;
   wherein the first surface region has a first center and wherein the second surface region has a second center; and
   wherein the first and second centers of the surface regions are separate and are separated by no more than 5 mm, and the first and second pulses are sequential and separated by no more than 30 seconds, and wherein the first and second pulses of the cryogenic fluid are effective to cause a lysis of tissue of the first and second surface regions, respectively.

2. The apparatus of claim 1, wherein the electronic image acquisition system is configured to identify a type of lesion as at least one of an age spot, a wart, and a melasma, and wherein the information comprises the type of lesion.

3. The apparatus of claim 1, wherein the centers of the regions are separated by no more than 2 mm.

4. The apparatus of claim 1, wherein the centers of the regions are separated by no more than 1 mm.

5. The apparatus of claim 1, wherein the first and second pulses are separated by no more than 20 seconds.

6. The apparatus of claim 1, wherein the first and second pulses are separated by no more than 10 seconds.

7. The apparatus of claim 1, further comprising a spacer that passively maintains a nearly constant distance between the nozzle and the lesion.

8. The apparatus of claim 1, further comprising first and second optical beams that operate in conjunction with the electronic image acquisition system to provide the controller with z-axis information relative to the first and second surfaces of the lesion.

9. The apparatus of claim 1, wherein the positioner comprises an arm that provides for three-dimensional movement of the nozzle.

10. The apparatus of claim 1 wherein the controller analyzes a change in at least one of a coloration and a temperature of at least one of the first and second surface regions of the lesion.

11. The apparatus of claim 1, further comprising a mechanism that causes physical rotation of the lesion.

12. The apparatus of claim 1, further comprising a second nozzle configured to dispense the cryogenic fluid at a third surface region of the lesion.

13. The apparatus of claim 1 further comprising a sensor configured to monitor a movement of the lesion, and provide feedback to a controller.

14. The apparatus of claim 1 wherein the cryogenic fluid is selected from the list consisting of liquid carbon dioxide, difluoroethane, dichloro difluoro methane, and tetrafluoroethane.

15. The apparatus of claim 1, where the first and second surface regions of the lesion overlap.

16. The apparatus of claim 1, wherein the lysis of tissue of the first and second surface regions is a result of the first and second pulses lowering a temperature of the first and second surface regions, respectively.

* * * * *